(12) United States Patent
Nagai et al.

(10) Patent No.: US 7,951,536 B2
(45) Date of Patent: May 31, 2011

(54) METHOD FOR DETERMINING BASE SEQUENCE OF DNA

(75) Inventors: Takeharu Nagai, Hokkaido (JP); Tomomi Tani, Hokkaido (JP); Ippei Kotera, Hokkaido (JP); Yohihiro Yoneda, Osaka (JP)

(73) Assignees: National University Corporation Hokkaido University, Hokkaido (JP); Nikon Corporation, Tokyo (JP)

( * ) Notice: Subject to any disclaimer, the term of this patent is extended or adjusted under 35 U.S.C. 154(b) by 39 days.

(21) Appl. No.: 12/279,924

(22) PCT Filed: Feb. 20, 2007

(86) PCT No.: PCT/JP2007/053461
§ 371 (c)(1),
(2), (4) Date: Oct. 20, 2008

(87) PCT Pub. No.: WO2007/097443
PCT Pub. Date: Aug. 30, 2007

(65) Prior Publication Data
US 2010/0009354 A1 Jan. 14, 2010

(30) Foreign Application Priority Data
Feb. 20, 2006 (JP) ................................. 2006-043211

(51) Int. Cl.
*C12Q 1/68* (2006.01)
*C07H 21/02* (2006.01)
*C07H 21/04* (2006.01)

(52) U.S. Cl. ........................... 435/6; 536/23.1; 536/24.3

(58) Field of Classification Search ..... 435/6; 536/23.1, 536/24.3
See application file for complete search history.

(56) References Cited

U.S. PATENT DOCUMENTS

| | | | |
|---|---|---|---|
| 5,552,278 A * | 9/1996 | Brenner | 435/6 |
| 5,846,719 A | 12/1998 | Brenner et al. | |
| 2001/0036672 A1* | 11/2001 | Anderson et al. | 436/180 |
| 2001/0053526 A1* | 12/2001 | Lipshutz et al. | 435/6 |
| 2002/0172965 A1* | 11/2002 | Kamb et al. | 435/6 |
| 2004/0005564 A1* | 1/2004 | Mauro et al. | 435/6 |
| 2009/0305248 A1* | 12/2009 | Lander et al. | 435/6 |

FOREIGN PATENT DOCUMENTS

| | | |
|---|---|---|
| JP | 8-511174 A | 11/1996 |
| JP | 2000-515006 A | 11/2000 |
| JP | 2002-532104 A | 10/2002 |
| WO | WO 00/36152 A1 | 6/2000 |
| WO | WO 2005/038026 A1 | 4/2005 |

OTHER PUBLICATIONS

Szybalski et al. Class-IIS restriction enzymes—a review. Gene 100: 13-26 (1991).*
Crut et al., "Detection of single DNA molecules by multicolor quantum-dot end-labeling," Nucleic Acids Research, 2005, 33(11):e98, 9 pages.
Brenner et al., "Gene expression analysis by massively parallel signature sequencing (MPSS) on microbead arrays," Nature Biotechnology, Jun. 2000, 18:630-634.

* cited by examiner

*Primary Examiner* — Ethan Whisenant
(74) *Attorney, Agent, or Firm* — Foley & Lardner LLP

(57) ABSTRACT

The present invention provides a method for determining the base sequence of a DNA. According to the method for determining the base sequence of a DNA of the present invention, a probe is used, which is a probe having a protruding end and identification-labeled according to the species of the base at the protruding end, containing a recognition sequence of a class IIS restriction enzyme, to carry out simultaneously in a chain reaction, for a plurality of DNAs to be analyzed, ligation of the end base of a DNA to be analyzed and a probe and cleavage of the end base of the DNA to be analyzed, allowing the base sequence to be determined sequentially by a single molecule spectrofluorimetry method, such that an effective determination of the base sequence of a DNA becomes possible.

24 Claims, 5 Drawing Sheets

Fig. 2
(1)
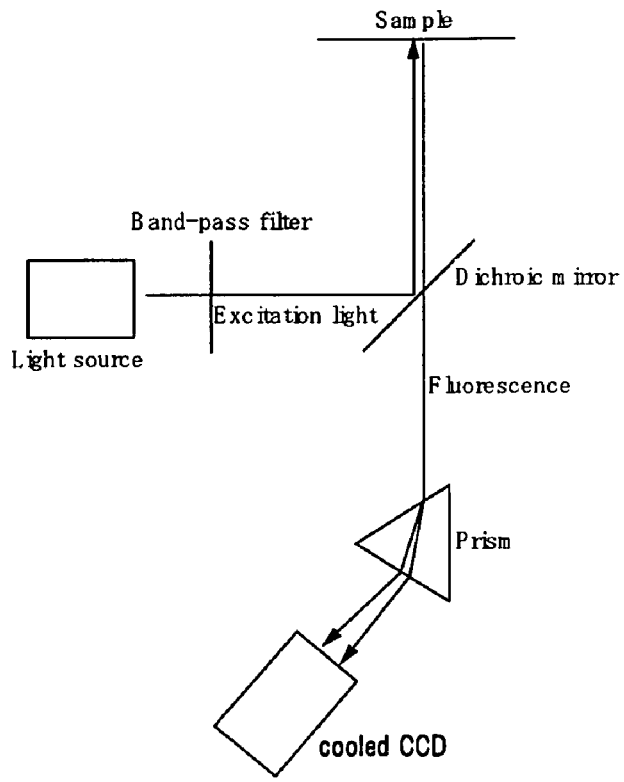
(2)
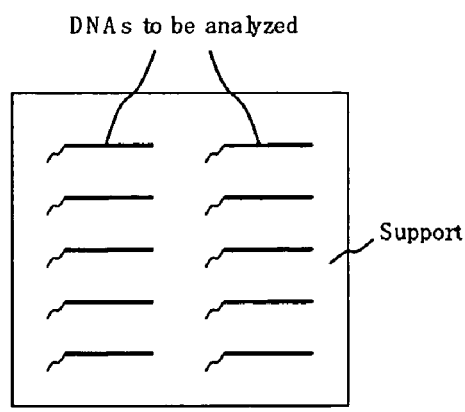
Fig. 3
biotin-GCTACGTAAGCTTCATGAATTCGACACTGTGTCAGCA
        CGATGCATTCGAAGTACTTAAGCTGTGACACAGTCG (1a) CGTCCCAGTACTAGTATGC
CGCAGGGTCATGATCATACG-amine (1b) CGTCCCAGTACTAGTATGC
TGCAGGGTCATGATCATACG-amine (2) biotin-ACTCGGCATGCGCCAGAGAGAGAGAGAG
TGAGCCGTACGCGGTCTCTCTCTCTCT (1)

(2)

(1)

(2)

(3)

SEQUENCE LISTING

```
<160> NUMBER OF SEQ ID NOS: 24

<210> SEQ ID NO 1
<211> LENGTH: 19
<212> TYPE: DNA
<213> ORGANISM: Artificial
<220> FEATURE:
<223> OTHER INFORMATION: synthetic polynucleotide (complementary to
      SEQ ID NO:2)

<400> SEQUENCE: 1
cgtcccagta ctagtatgc                                                 19

<210> SEQ ID NO 2
<211> LENGTH: 20
<212> TYPE: DNA
<213> ORGANISM: Artificial
<220> FEATURE:
<223> OTHER INFORMATION: synthetic polynucleotide (complementary to
      SEQ ID NO:1)

<400> SEQUENCE: 2
gcatactagt actgggacgt                                                20

<210> SEQ ID NO 3
<211> LENGTH: 19
<212> TYPE: DNA
<213> ORGANISM: Artificial
<220> FEATURE:
<223> OTHER INFORMATION: synthetic polynucleotide (complementary to
      SEQ ID NO:4)

<400> SEQUENCE: 3
cgtcccagta ctagtatgc                                                 19

<210> SEQ ID NO 4
<211> LENGTH: 20
<212> TYPE: DNA
<213> ORGANISM: Artificial
```

```
<220> FEATURE:
<223> OTHER INFORMATION: synthetic polynucleotide (complementary to
      SEQ ID NO:3)

<400> SEQUENCE: 4
gcatactagt actgggacga                                              20

<210> SEQ ID NO 5
<211> LENGTH: 19
<212> TYPE: DNA
<213> ORGANISM: Artificial
<220> FEATURE:
<223> OTHER INFORMATION: synthetic polynucleotide (complementary to
      SEQ ID NO:6)

<400> SEQUENCE: 5
cgtcccagta ctagtatgc                                               19

<210> SEQ ID NO 6
<211> LENGTH: 20
<212> TYPE: DNA
<213> ORGANISM: Artificial
<220> FEATURE:
<223> OTHER INFORMATION: synthetic polynucleotide (complementary to
      SEQ ID NO:5)

<400> SEQUENCE: 6
gcatactagt actgggacgc                                              20

<210> SEQ ID NO 7
<211> LENGTH: 19
<212> TYPE: DNA
<213> ORGANISM: Artificial
<220> FEATURE:
<223> OTHER INFORMATION: synthetic polynucleotide (complementary to
      SEQ ID NO:8)

<400> SEQUENCE: 7
cgtcccagta ctagtatgc                                               19

<210> SEQ ID NO 8
<211> LENGTH: 20
<212> TYPE: DNA
<213> ORGANISM: Artificial
<220> FEATURE:
<223> OTHER INFORMATION: synthetic polynucleotide (complementary to
      SEQ ID NO:7)

<400> SEQUENCE: 8
gcatactagt actgggacgg                                              20

<210> SEQ ID NO 9
<211> LENGTH: 37
<212> TYPE: DNA
<213> ORGANISM: Artificial
<220> FEATURE:
<223> OTHER INFORMATION: synthetic polynucleotide (complementary to
      SEQ ID NO:10)

<400> SEQUENCE: 9
gctacgtaag cttcatgaat tcgacactgt gtcagca                           37

<210> SEQ ID NO 10
<211> LENGTH: 36
<212> TYPE: DNA
<213> ORGANISM: Artificial
```

```
<220> FEATURE:
<223> OTHER INFORMATION: synthetic polynucleotide (complementary to
      SEQ ID NO:9)

<400> SEQUENCE: 10
gctgacacag tgtcgaattc atgaagctta cgtagc                              36

<210> SEQ ID NO 11
<211> LENGTH: 19
<212> TYPE: DNA
<213> ORGANISM: Artificial
<220> FEATURE:
<223> OTHER INFORMATION: probe

<400> SEQUENCE: 11
cgtcccagta ctagtatgc                                                 19

<210> SEQ ID NO 12
<211> LENGTH: 20
<212> TYPE: DNA
<213> ORGANISM: Artificial
<220> FEATURE:
<223> OTHER INFORMATION: probe

<400> SEQUENCE: 12
gcatactagt actgggacgc                                                20

<210> SEQ ID NO 13
<211> LENGTH: 19
<212> TYPE: DNA
<213> ORGANISM: Artificial
<220> FEATURE:
<223> OTHER INFORMATION: probe

<400> SEQUENCE: 13
cgtcccagta ctagtatgc                                                 19

<210> SEQ ID NO 14
<211> LENGTH: 20
<212> TYPE: DNA
<213> ORGANISM: Artificial
<220> FEATURE:
<223> OTHER INFORMATION: probe

<400> SEQUENCE: 14
gcatactagt actgggacgt                                                20

<210> SEQ ID NO 15
<211> LENGTH: 30
<212> TYPE: DNA
<213> ORGANISM: Artificial
<220> FEATURE:
<223> OTHER INFORMATION: synthetic polynucleotide (complementary to
      SEQ ID NO:16)

<400> SEQUENCE: 15
actcggcatg cgccagagag agagagagag                                     30

<210> SEQ ID NO 16
<211> LENGTH: 29
<212> TYPE: DNA
<213> ORGANISM: Artificial
<220> FEATURE:
<223> OTHER INFORMATION: synthetic polynucleotide (complementary to
      SEQ ID NO:15)
```

-continued

<400> SEQUENCE: 16
tctctctctc tctctggcgc atgccgagt                                      29

<210> SEQ ID NO 17
<211> LENGTH: 47
<212> TYPE: DNA
<213> ORGANISM: Artificial
<220> FEATURE:
<223> OTHER INFORMATION: probe

<400> SEQUENCE: 17
tgcctgacat gtgtacgtct cgattagcac gaagtcagga tgcagtg                  47

<210> SEQ ID NO 18
<211> LENGTH: 50
<212> TYPE: DNA
<213> ORGANISM: Artificial
<220> FEATURE:
<223> OTHER INFORMATION: probe

<400> SEQUENCE: 18
agttcactgc atcctgactt cgtgctaatc gagacgtaca catgtcagga               50

<210> SEQ ID NO 19
<211> LENGTH: 47
<212> TYPE: DNA
<213> ORGANISM: Artificial
<220> FEATURE:
<223> OTHER INFORMATION: probe

<400> SEQUENCE: 19
tgcctgacat gtgtacgtct cgattagcac gaagtcagga tgcagtg                  47

<210> SEQ ID NO 20
<211> LENGTH: 50
<212> TYPE: DNA
<213> ORGANISM: Artificial
<220> FEATURE:
<223> OTHER INFORMATION: probe

<400> SEQUENCE: 20
agtacactgc atcctgactt cgtgctaatc gagacgtaca catgtcagga               50

<210> SEQ ID NO 21
<211> LENGTH: 47
<212> TYPE: DNA
<213> ORGANISM: Artificial
<220> FEATURE:
<223> OTHER INFORMATION: probe

<400> SEQUENCE: 21
tgcctgacat gtgtacgtct cgattagcac gaagtcagga tgcagtg                  47

<210> SEQ ID NO 22
<211> LENGTH: 50
<212> TYPE: DNA
<213> ORGANISM: Artificial
<220> FEATURE:
<223> OTHER INFORMATION: probe

<400> SEQUENCE: 22
agtccactgc atcctgactt cgtgctaatc gagacgtaca catgtcagga               50

```
<210> SEQ ID NO 23
<211> LENGTH: 47
<212> TYPE: DNA
<213> ORGANISM: Artificial
<220> FEATURE:
<223> OTHER INFORMATION: probe

<400> SEQUENCE: 23
tgcctgacat gtgtacgtct cgattagcac gaagtcagga tgcagtg          47

<210> SEQ ID NO 24
<211> LENGTH: 50
<212> TYPE: DNA
<213> ORGANISM: Artificial
<220> FEATURE:
<223> OTHER INFORMATION: probe

<400> SEQUENCE: 24
agtgcactgc atcctgactt cgtgctaatc gagacgtaca catgtcagga        50
```

METHOD FOR DETERMINING BASE SEQUENCE OF DNA

CROSS-REFERENCE TO RELATED APPLICATIONS

This application is a National Stage application of PCT/JP2007/053461, filed Feb. 20, 2007, which claims priority from Japanese application JP 2006-043211, filed Feb. 20, 2006.

TECHNICAL FIELD

The present invention relates to a method for determining the base sequence of a DNA. More specifically, the present invention relates to a method in which a DNA base deletion chain reaction by a restriction enzyme and a DNA ligase is detected at a single molecule level to determine the base sequence of a DNA.

BACKGROUND

From prior art, the Maxam-Gilbert method and the Sanger method are known as methods for determining the base sequence of a DNA. For instance, in the Maxam-Gilbert method, steps such as the following are required, for example, to determine the base sequence of a DNA.

(1) Fragmenting DNA extracted from cells and integrating a DNA fragment into *Escherichia coli*, or the like, using a gene recombination technique, or the like.

(2) Culturing *Escherichia coli*, or the like, to amplify the integrated DNA fragment (cloning).

(3) Lysing *Escherichia coli* or the like, separating biochemically the integrated DNA fragment, and carrying out of DNA purification with high purity.

(4) Based on the purified DNA fragment, preparing DNA fragments that are different in length by one base each, using the PCR technique. In this step, four species of label are added to the DNA fragments corresponding to the four species of base.

(5) Purifying the reaction product of (4).

(6) Separating by electrophoresis according to the molecular weight of the DNA fragments that are different in length by one base each, and detecting the fluorescence to determine the base sequence of DNA.

Although such method as described above requires cloning, the length of a DNA fragment that can be cloned at once is from several thousands to several tens of thousands base pairs. Consequently, in order to determine, for instance, the base sequence of the total genome for a human, which is approximately three billion base pairs, cloning on the order of at least 100,000 times is necessary.

Thus, with the DNA base sequence determination method that has been used in prior art, there is the problem that considerable effort and time, and enormous costs are necessary in order to determine the base sequence of a DNA. In particular, since the genomic information of higher organisms reach as high as several billions of base pairs, national projects have been necessary, for instance, to determine the base sequence of the total genomic DNA of one human.

DISCLOSURE OF THE INVENTION

Under such circumstances, the development of a method allowing the base sequence of a DNA to be determined in a short time, without requiring cumbersome manipulations, is desirable. In addition, the development of a DNA base sequence determination method that does not require cloning is desirable.

As a result of earnest studies to solve the above problems, the present inventors discovered that the base sequence of a DNA extracted from cells could be determined without cloning, by using a probe, which is a probe having a one-base-protruding end and identification-labeled according to the species of the base at the protruding end, containing a recognition sequence of a restriction enzyme whose recognition sequence is apart from the cleavage site, and completed the present invention.

That is to say, the present invention provides such DNA base sequence determination method, probe, kit for the determination of the base sequence of a DNA, and the like, as follows.

(1) A method for determining the base sequence of a DNA, comprising:

(a) the step of ligating a DNA to be analyzed, wherein said DNA has a protruding end and is immobilized on a support, and a probe by a DNA ligase, wherein said probe has a protruding end and identification-label according to the species of the base at the protruding end, and said probe contains a recognition sequence of a restriction enzyme whose recognition sequence is apart from a cleavage site;

(b) the step of identifying the species of the identification label of said probe that has been ligated to said DNA to be analyzed; and (c) the step of cleaving a ligated DNA of said DNA to be analyzed and said probe by said restriction enzyme whose recognition sequence is apart from the cleavage site.

(2) The method according to (1) above, wherein the protruding end of said DNA to be analyzed and the protruding end of said probe are both one-base-protruding ends.

(3) The method according to (1) or (2) above, wherein said probe includes four species of probe having a one base- or a two base-protruding end complementary respectively to A, T, C or G.

(4) The method according to (2) or (3) above, wherein the distance between the recognition sequence for said restriction enzyme and the protruding end on said probe is one base shorter than the distance between the recognition sequence and the cleavage site for said restriction enzyme.

(5) The method according to any of (1) to (4) above, wherein each of the steps is carried out by a chain reaction.

(6) The method according to any of (1) to (5) above, wherein said identification label is a fluorescent label, a quantum dot or a metal colloid.

(7) The method according to any of (1) to (6) above, wherein identification of the species of said identification label is carried out by single molecule observation.

(8) The method according to (6) above, wherein identification of the species of said identification label is carried out by detection of fluorescence wavelength of said fluorescent label.

(9) The method according to (8) above, wherein the detection of the fluorescence wavelength is carried out using a single molecule fluorescence spectromicroscope.

(10) The method according to any of (1) to (9) above, wherein the base sequences of a plurality of DNAs to be analyzed are determined simultaneously.

(11) The method according to any of (1) to (10) above, wherein said restriction enzyme is an enzyme that generates a one base- or a two base-protruding end.

(12) The method according to (11) above, wherein said enzyme is a class IIS restriction enzyme.

(13) The method according to any of (1) to (12) above, wherein the protruding end of said DNA to be analyzed and the protruding end of said probe are both 3' protruding ends.

(14) The method according to any of (1) to (13) above, wherein said restriction enzyme is an enzyme that generates a one base- or a two base-protruding end at the 3' end.

(15) The method according to (14) above, wherein said enzyme is selected from BmrI, BmuI, BfiI, AsuHPI, HphI, BciVI, BfuI, HpyAV, MboII, NcuI, MnlI, Asp26HI, Asp27HI, Asp35HI, Asp36HI, Asp40HI, Asp50HI, Bce83I, BcgI, BmaHT, BpmI, BpuEI, BsaMI, BscCI, Bse1I, Bse3DI, BseGI, BseMI, BseNI, BsgI, BsmI, BspKT5I, BsrI, BsrDI, BsrSI, Bst11I, BstF5I, BtsI, BtsCT, CspCI, CstMI, EciI, Eco57MI, GsuI, Mva1269I, PctI, Tsp1I, TspDTI and TspGWI.

(16) The method according to any of (1) to (12) above, wherein the protruding end of said DNA to be analyzed and the protruding end of said probe are both 5' protruding ends.

(17) The method according to any of (1) to (12) and (16) above, wherein said restriction enzyme is an enzyme that generates a one base- or a two base-protruding end at the 5' end.

(18) The method according to (17), wherein said enzyme is selected from AclWI, AlwI, BinI, BspPT, BstH9I, Bst31TI, EacI, BccI, HpyC1I, BcefI, PleI, PpsI, AciI, BceAI, Bme585I, BscAI, Bst19I, BstFZ438I, FauI, SmuI and SsiI.

(19) The method according to any of (1) to (18) above, wherein said support is formed from a material that is transparent to light.

(20) A probe, which is a probe having a protruding end and identification-labeled according to the species of the base at the protruding end, containing a recognition sequence of a restriction enzyme whose recognition sequence is apart from a cleavage site.

(21) The probe according to (20) above, wherein said protruding end is a one base- or a two base-protruding end.

(22) The probe according to (21) above, wherein the distance between said recognition sequence and said one-base-protruding end is one base shorter than the distance between said recognition sequence and said cleavage site.

(23) The probe according to any of (20) to (22) above, wherein said protruding end is a 3' protruding end.

(24) The probe according to any of (20) to (22) above, wherein said protruding end is a 5' protruding end.

(25) The probe according to any of (20) to (24) above, wherein said recognition sequence is a recognition sequence of a class IIS restriction enzyme.

(26) A kit for determining the base sequence of a DNA, containing the probe according to any of (20) to (25) above.

(27) The kit according to (26) above, wherein said probe includes at least four species of probe having a one base- or a two base-protruding end complementary respectively to A, T, C or G.

(28) The kit according to (26) or (27), further containing a restriction enzyme and a DNA ligase.

(29) A device for determining the base sequence of a DNA, comprising:
(i) a measurement cell,
(ii) optical means,
(iii) means for converting optical information into an identification signal, and
(iv) means for converting the identification signal into base sequence information; the interior of said measurement cell being provided with:

(a) means for ligating a DNA to be analyzed, which has a protruding end and is immobilized on a support, and a probe by a DNA ligase, wherein said probe has a protruding end and identification-label according to the species of the base at the protruding end, and said probe contains a recognition sequence of a restriction enzyme whose recognition sequence is apart from a cleavage site; and (c) means for cleaving a ligated DNA of said DNA to be analyzed and said probe by said restriction enzyme whose recognition sequence is apart from the cleavage site.

The present invention has the following effects.

(1) The base sequence determination of a DNA can be carried out extremely rapidly.

(2) DNA extracted from cells can be observed directly. That is to say, as described later, cloning is not necessary.

(3) It can be realized with a relatively small and simple device.

From the characteristics in (1) and (2), the time required for the determination of an entire genomic base sequence can be shortened drastically, allowing revolutionary changes to be brought to numerous fields such as genomic biology, genetics, medical science, pharmacology and the like. In addition, from the characteristics in (2) and (3), broad applications in clinical field can also be considered. For example, in regard to diseases involving a gene (for instance, diseases involving gene mutation, polymorphism (for instance, SNPs or the like) and so on), use is possible to medical treatments that are tailor-made according to the genomic information of each patient, one by one.

BRIEF DESCRIPTION OF THE DRAWINGS

FIG. 2 is an overview to explain the identification method for fluorescent label, and the like.

FIG. 3 is a figure showing the structure of biotinylated DNA comprising the DNA to be analyzed conjugated with biotin, used in Example 1.

BEST MODE FOR CARRYING OUT THE INVENTION

Figure 1:
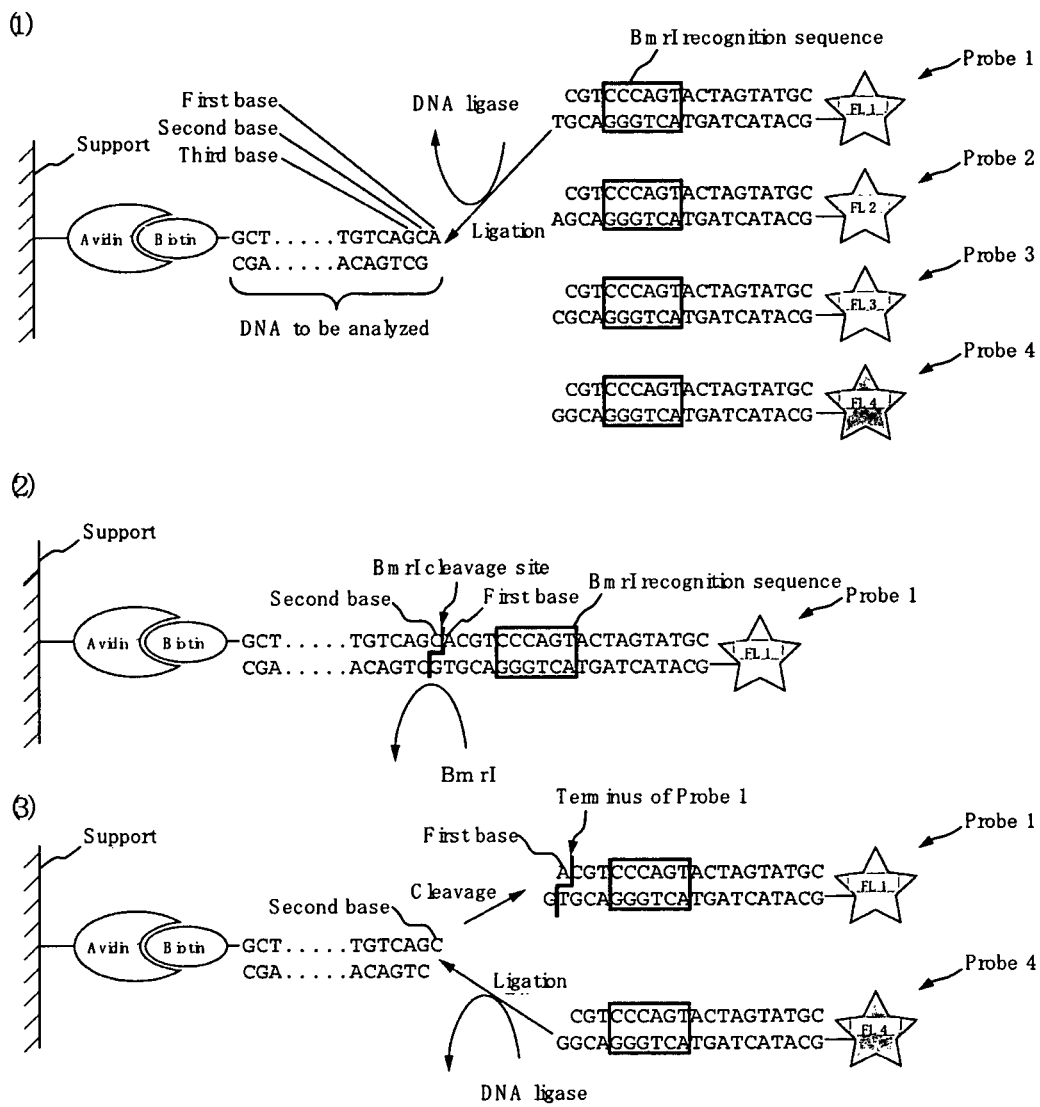
FIG. 1 is an overview to explain one embodiment of the present invention.

The present invention relates to a probe, which is a probe having a one base-protruding end and identification-labeled according to the species of the base at the protruding end, containing a recognition sequence of a restriction enzyme whose recognition sequence is apart from the cleavage site, a base sequence determination method for DNA using the probe, a kit for the base sequence determination of a DNA containing the probe, and the like.

Hereinafter, the present invention will be described in detail.

1. Base Sequence Determination Method for DNA

The first mode of the present invention relates to a base sequence determination method for DNA, having the Steps (a) to (c) described below:

(a) the step of ligating a DNA to be analyzed, which has a protruding end and is immobilized on a support, and a probe by a DNA ligase, wherein said probe has a protruding end and identification-label according to the species of the base at the protruding end, and said probe contains a recognition sequence of a restriction enzyme whose recognition sequence is apart from the cleavage site;

(b) the step of identifying the species of the identification label of the probe that has been ligated to the DNA to be analyzed; and (c) the step of cleaving the ligated DNA of the DNA to be analyzed and the probe by a restriction enzyme whose recognition sequence is apart from the cleavage site.

Hereinafter, the details of each step will be described.

(1) Step (a): Ligating the DNA to be Analyzed and the Probe with a DNA Ligase

Step (a) is a step for ligating the DNA to be analyzed and the probe with a DNA ligase. (DNA to be Analyzed)

The DNA to be the subject of the analysis, is not limited in particular, and can be derived from genomic DNA or can be derived from cDNA. Since the base sequence determination method for DNA of the present invention allows the base sequence of a single molecule of DNA to be determined without cloning, it can be used particularly preferably for determining the base sequence of genomic DNA extracted from cells. That is to say, a DNA derived from genomic DNA can be used preferably as DNA to be analyzed.

The length of the DNA to be analyzed is not limited in particular, and is, in general 1 to 5000 bases, preferably 2 to 1000 bases, more preferably 5 to 500 bases and particularly preferably 10 to 100 bases.

Preparation of the DNA to be Analyzed of the present invention can be carried out according to methods described in experiment manuals such as Molecular Cloning: A Laboratory Manual, Third Edition, Cold Spring Harbor Laboratory Press (2001) (hereinafter, abbreviated as Molecular Cloning, 3d Edition), Current Protocols in Molecular Biology, Supplements 1 to 38, John Wiley and Sons (1987-1997), DNA Cloning 1: Core Techniques, A practical Approach, Second Edition, Oxford University Press (1995). Specifically, for instance, when using DAN derived from genomic DNA, first, genomic DNA is prepared by extracting and purifying DNA from the tissue or cells of a living organism that will be the subject of analysis. Next, DNA fragments are prepared by cleaving the genomic DNA using a restriction enzyme or the like. The DNA fragments obtained in this way can be used as a DNA to be analyzed of the present invention, without cloning.

The DNA to be analyzed is immobilized onto a support. The support may be one that does not inhibit base sequence determination, and is not limited in particular. As a support, a support that immobilizes a biological molecule can be used, for instance, substrates such as glass substrate, quartz glass substrate, quartz substrate, silicon substrate, plastic substrate and metal substrate (for instance, gold foil substrate); containers such as glass container, quartz glass container and plastic container; membrane comprising materials such as nitrocellulose and polyvinylidene fluoride (PVDF), and the like, can be included. In order to immobilize a plurality of DNAs to be analyzed and carry out base sequence determination of a plurality of DNAs to be analyzed simultaneously, the support is preferably plate-shaped and, for instance, glass substrate, quartz glass substrate, silicon substrate, aluminum substrate, single crystal substrate transparent to light (for instance, $Al_2O_3$ and $SiO_2$) and the like, can be included. When a fluorescent substance is used for the identification-labeling of a probe, described later, as supports, those transparent to light are preferred, furthermore, that are transparent to light and plate-shaped are preferred, and in particular, glass substrate, quartz glass substrate, silicon substrate, single crystal substrate transparent to light (for instance, $Al_2O_3$ and $SiO_2$) are preferred, among which glass substrate is preferred.

Means for immobilizing the DNA to be analyzed onto a support suffices to be means that does not impede the base sequence determination of DNA to be analyzed, and means immobilizing directly or indirectly can be used. Preferably, indirect immobilization is possible using the linking portions provided on the DNA to be analyzed and the support. As such linking portion, a combination of substances that form an affinity bond, a chemical bond using a crosslinking agent, or the like, can be used. As combination of substances that form an affinity bond, for instance, combinations such as avidin or streptavidin/biotin, and antibody or antibody fragment/antigenic molecule (epitope) may be included, and the combination of avidin or streptavidin/biotin is used preferably. When such a combination of substance that from an affinity bond is used, one substance on one hand of the combination is bonded to the support (or is originally a part thereof), and the substance on the other hand is bonded to the DNA to be analyzed. Preferably, avidin or streptavidin is bonded to the support (or is originally a part thereof), and biotin is bonded to the DNA to be analyzed. These are brought into contact, and avidin or streptavidin and biotin form an affinity bond, immobilizing the DNA to be analyzed onto the support.

The site for immobilizing the DNA to be analyzed onto the support may be a site that does not inhibit the base sequence determination of the DNA to be analyzed, is not limited in particular, and is preferably the opposite end to the protruding end (that is to say end where the probe becomes connected).

There is no particular limitation on the number of DNAs to be analyzed that are immobilized on the support. In the present invention, for instance, 1 to approximately 100, approximately 100 to approximately 1000, approximately 1000 to approximately 10,000, approximately 10,000 to approximately 50,000, approximately 50,000 to approximately 100,000, approximately 100,000 to approximately 500,000 of DNAs to be analyzed can be immobilized onto the support and processed. From the point of view of rapidly determining the base sequence, the number of DNA to be analyzed that are immobilized on the support is preferably 100 or greater.

A protruding end is formed at the end of the DNA to be analyzed that is not immobilized. The protruding end is formed in such a way that the probe to be used can be connected. Specifically, when a probe having a 3' protruding end is used, the protruding end of the DNA to be analyzed is also a 3' protruding end. When a probe having a 5' protruding end is used, the protruding end of the DNA to be analyzed is also a 5' protruding end. When a probe has a one base-protruding end, the protruding end of the DNA to be analyzed is also a one base-protruding end. If the probe has a two bases protrusion or greater, accordingly, the DNA to be analyzed has also a two bases protrusion or greater. More Specifically, when a probe having a 3' protruding end with a one base protrusion, the protruding end of the DNA to be analyzed is also a 3' protruding end with a one base protrusion. When a probe having a 5' protruding end with a one base protrusion, the protruding end of the DNA to be analyzed is also a 5' protruding end having a one base protrusion.

Such protruding ends can be formed using suitable restriction enzymes. For instance, if a recognition sequence of the restriction enzyme used in Step (c) described later is contained within the DNA to be analyzed, a protruding end can be formed using a restriction enzyme that recognizes the same sequence as the recognition sequence of the restriction enzyme used in Step (c), the protruding end may be formed by the restriction enzyme used in Step (c). Formation of the protruding end of the DNA to be analyzed is carried out preferably after the DNA to be analyzed has been immobilized onto the support.

Note that, if a recognition sequence of the restriction enzyme used in Step (c) is contained within the DNA to be analyzed, in Step (c), the restriction enzyme recognizes this recognition sequence and cleaves the DNA to be analyzed, which impedes base sequence determination. Therefore, prior to carrying out Step (a), pre-processing with the restriction enzyme used in Step (c) or the like, it is preferable to carry out a treatment to avoid the cleavage of the DNA to be analyzed.

(Probe)

The probe of the present invention contains a protruding end, an identification label according to the species of the base at the protruding end, and a recognition sequence of a restriction enzyme. The probe of the present invention may be a probe comprising two single-stranded DNA that have been annealed (in the present description, may be designated "bimolecular probe"), or may be a probe having a hairpin structure comprising one single-stranded DNA that has been annealed intramolecularly (in the present description, may be designated "monomolecular probe"). As bimolecular probes, those labeled at the terminus that is on the opposite side from the protruding end or from the end on the side of the cleavage site of the restriction enzyme, is preferred. If the end of the probe is to be labeled, the labeled end may be either of 5' end or 3' end. As monomolecular probes, those with the hairpin structure portion labeled are preferable.

The protruding end of the probe to be used is one that has the same strand of protruding end (5' or 3') and number of bases in the protruding end as the protruding end of the DNA to be analyzed. Specifically, for instance, if the protruding end of the DNA to be analyzed is a 3' protruding end with a one base protrusion, a probe having a 3' protruding end with a one base protrusion is used. If the protruding end of the DNA to be analyzed is a 5' protruding end with a one base protrusion, a probe having a 5' protruding end with a one base protrusion is used. The bases at the protruding end of the probe to be used are bases that are complementary to the bases that may form the protruding end of the DNA that is to be the subject of analysis. Specifically, when the protruding end is a one base-protruding end, for instance, four species of probe, in which the base at the protruding end is adenine (A), thymine (T), cytosine (C) or guanine (G), are used. When the protruding end is a two base-protruding end, for instance, 16 species of probe, in which the bases at the protruding end are AA, AT, AC, AG, TA, TT, TC, TG, CA, CT, CC, CG, GA, GT, GC or GG, are used. Since when the number of protruding bases increase, the species of probe to be used become numerous, and the identification labeling and identification of each probe tend to be difficult, such that the protruding end is preferably a one- or a two base-protruding end, and in particular a one base-protruding end is preferred. Alternatively, four species of probe having a two base-protruding end, i.e., NA, NT, NG and NC, can be prepared and be read one base at a time. As such probes, probes in which the terminus side is N (that is to say, NA, NT, NG, NC with the left side as the terminus), probes in which the terminus side is A, T, G or C (that is to say, AN, AT, AG, AC with the left side as the terminus) may be included, although an terminus side of N is preferable on the point that the base sequence of the DNA to be analyzed can be determined from the terminus. Here, N represents a base site where, during the oligo-DNA synthesis to from the probe, one in which adenine (A), thymine (T), cytosine (C) or guanine (G) were mixed was incorporated, with one in which adenine (A), thymine (T), cytosine (C) and guanine (G) were mixed in identical proportions being preferred. That is to say, it is preferable that any base among adenine (A), thymine (T), cytosine (C) or guanine (G) is present with the same probability at the site of N.

Probes having a protruding end of 3 bases or more, alternatively to NA, NT, NG and NC, can also be used preferably, such as, probes having a 3 base-protruding end such as NNA, NNT, NNG and NNC, probes having a 4 base-protruding end such as NNNA, NNNT, NNNG and NNNC. Such probe having a protruding end of 3 bases or more is preferable on the point that efficiency of annealing is satisfactory. However, if the number of bases in the protruding end becomes too large, the possibility of misannealing tends to become higher. Thus, from the points of annealing efficiency and avoidance of misannealing, probes having a 3 to 5 base-protruding end is preferred, and in particular probes having a 4 base-protruding end is preferred.

As labeling substances used in identification of labeling, a labeling substance allowing the base at the protruding end to be identified is sufficient. As labeling substances, various labeling substances such as, for instance, fluorescent substances, chemiluminescent substances and labeling substances that may measure a change in polarization, can be used, among which fluorescent substances are preferably used. The fluorescent substance used in the present invention is not limited in particular as long as the labeling with the fluorescent substance is detectable. As fluorescent substances, fluorescent substances used for labeling of nucleic acids can be used, for instance, rhodamine B, rhodamine 6G, x-rhodamine, tetramethyl rhodamine (TMR), tetramethyl rhodamine isothiocyanate (TMRITC), fluorescein, fluorescein isothiocyanate (FITC), Cy (registered trade mark)$_3$, Cy (registered trade mark)$_5$, TAMRA (registered trade mark), Alexa Fluor (registered trade mark) 350, Alexa Fluor (registered trade mark) 405, Alexa Fluor (registered trade mark) 430, Alexa Fluor (registered trade mark) 488, Alexa Fluor (registered trade mark) 532, Alexa Fluor (registered trade mark) 546, Alexa Fluor (registered trade mark) 555, Alexa Fluor (registered trade mark) 568, Alexa Fluor (registered trade mark) 594, Alexa Fluor (registered trade mark) 633, Alexa Fluor (registered trade mark) 647, Alexa Fluor (registered trade mark) 680, Alexa Fluor (registered trade mark) 700, Alexa Fluor (registered trade mark) 749, acridine yellow, texas red, quantum dots, fluorescent beads, TransFluoSpheres (registered trade mark) beads, metal colloid and the like, can be included. As quantum dots, for instance, Qdot (registered trade mark) 525 ITK™ Carboxyl Quantum Dots, Qdot (registered trade mark) 545 ITK™ Carboxyl Quantum Dots, Qdot (registered trade mark) 565 ITK™ Carboxyl Quantum Dots, Qdot (registered trade mark) 585 ITK™ Carboxyl Quantum Dots, Qdot (registered trade mark) 605 ITK™ Carboxyl Quantum Dots, Qdot (registered trade mark) 655 ITK™ Carboxyl Quantum Dots, Qdot (registered trade mark) 705 ITK™ Carboxyl Quantum Dots, Qdot (registered trade mark) 800 ITK™ Carboxyl Quantum Dots, Qdot (registered trade mark) 525 ITK™ Amino (PEG) Quantum Dots, Qdot (registered trade mark) 545 ITK™ Amino (PEG) Quantum Dots, Qdot (registered trade mark) 565 ITK™ Amino (PEG) Quantum Dots, Qdot (registered trade mark) 585 ITK™ Amino (PEG) Quantum Dots, Qdot (registered trade mark) 605 ITK™ Amino (PEG) Quantum Dots, Qdot (registered trade mark) 655 ITK™ Amino (PEG) Quantum Dots, Qdot (registered trade mark) 705 ITK™ Amino (PEG) Quantum Dots, Qdot (registered trade mark) 800 ITK™ Amino (PEG) Quantum Dots, Qdot (registered trade mark) 545 ITK™ Organic Quantum Dots, Qdot (registered trade mark) 565 ITK™ Organic Quantum Dots, Qdot (registered trade mark) 585 ITK™ Organic Quantum Dots, Qdot (registered trade mark) 605 ITK™ Organic Quantum Dots, Qdot (registered trade mark) 655 ITK™ Organic Quantum Dots, Qdot (registered trade mark) 705 ITK™ Organic Quantum Dots, Qdot (registered trade mark) 800 ITK™ Organic Quantum Dots and the like (hereabove, Invitrogen Corporation), quantum dots manufactured by Evident Thechnologies, and the like, can be included. Note that when the length of the DNA to be analyzed is long, the time required for analysis becomes long, such that using a fluorescent substance that is particularly difficult to bleach is preferred. In addition, using a bleach prevention agent according to the fluorescent dye is preferred.

So that the species of a base at the protruding end can be identified, the probes are labeled using labeling substances that are distinguishable from one another for each species of bases at the protruding end. Specifically, if the protruding end is a one base-protruding end, for instance, four species of probe respectively having a one base-protruding end that is complementary to four species of base (A, T, C, G) of a DNA are labeled using four species of labeling substance that are distinguishable from one another. If the protruding end is a two base-protruding end, it suffices that 16 species of probe having two base-protruding ends that are respectively complementary to the species of bases at a two base-protruding end of a DNA are labeled using 16 species of identification substance that are distinguishable from one another. When the protruding end of the probe is protruding by 3 bases or more, labeling with labeling substances that are distinguishable from one another for each species of the bases of the protruding end is sufficient. Labeling of probes can be carried out directly or indirectly by well known methods such as chemical modification.

The recognition sequence for a restriction enzyme contained in the probe has a base sequence that corresponds to the species of restriction enzyme used in Step (c) described later (restriction enzyme whose recognition sequence is apart from the cleavage site). Here, the restriction enzyme used in Step (c) is a restriction enzyme having a cleavage site that forms a protruding end having the same strand of protruding end (5' or 3') and number of bases in the protruding end as the protruding end of the probe to be used. Specifically, for instance, if the protruding end of the probe is a 3' protruding end with a one base protrusion, a restriction enzyme having a cleavage site generating a one base protrusion at the 3' end is used. If the protruding end of the probe is a 5' protruding end with a one base protrusion, a restriction enzyme having a cleavage site generating a one base protrusion at the 5' end is used.

The distance between the recognition sequence and the protruding end is shorter than the distance between the recognition sequence and the cleavage site of the restriction enzyme used in Step (c), by the number of bases determined at once in Step (b). Therefore, when the number of bases of the DNA protruding at the protruding end and the number of bases determined at once in Step (b) are equal, the distance between the recognition sequence and the protruding end is shorter than the distance recognition sequence and cleavage site for the restriction enzyme used in Step (c) by the number of bases of the DNA protruding at the protruding end. Specifically, for instance, if the protruding end is a one base-protruding end, the number of bases determined at once in Step (b) is also one base, such that the distance between the recognition sequence and the protruding end is one base shorter than the distance between the recognition sequence and the cleavage site. In addition, for instance, if the protruding end is a two base-protruding end, and the sequence is determined two bases at a time, the distance between the recognition sequence and the protruding end is two bases shorter than the distance between the recognition sequence and the cleavage site. Conversely, if a sequence is determined one base at a time even when the protruding end is a two base-protruding end using, for instance, probes having the two base-protruding ends NA, NT, NG and NC, a probe whose distance between the recognition sequence and the protruding end is one base shorter than the distance between the recognition sequence and the cleavage site is used.

In addition, the bases in a DNA to be analyzed can be analyzed two bases at a time (skipping one base) by using probes having one base-protruding ends, in which the distance between the recognition sequence and the protruding end is two bases shorter than the distance between the recognition sequence and the cleavage site.

In addition, the bases in the DNA to be analyzed can also be analyzed two bases at a time (skipping one base) by using probes having two base-protruding ends, for instance, NA, NT, NG and NC, in which the distance between the recognition sequence and the protruding end is two bases shorter than the distance between the recognition sequence and the cleavage site (that is to say, shorter by the same number of bases as the number of bases of the protruding ends).

Similarly, the bases in the DNA to be analyzed can also be analyzed four bases at a time (skipping 3 bases) by using a probes having four base-protruding ends, for instance, NNNA, NNNT, NNNG and NNNC, in which the distance between the recognition sequence and the protruding end is four bases shorter than the distance between the recognition sequence and the cleavage site (that is to say, shorter by the same number of bases as the number of bases of the protruding ends). The bases in the DNA to be analyzed can also be analyzed three or two bases at a time by using probes in which the distance between the recognition sequence and the protruding end is three or two bases shorter than the distance between the recognition sequence and the cleavage site. The bases in the DNA to be analyzed can also be analyzed five or six bases at a time by using a probe in which the distance between the recognition sequence and the protruding end is five or six bases shorter than the distance between the recognition sequence and the cleavage site. In this way, by using probes having n (n represents an integer of one or greater) base-protruding ends, in which the distance between the recognition sequence and the protruding end is m (m represents an integer of 2 or greater) bases shorter than the distance between the recognition sequence and the cleavage site, the bases in the DNA to be analyzed can be analyzed m bases at a time (skipping m−1 bases). As discussed above, when the bases in the DNA to be analyzed have been analyzed two bases or more at a time, the DNA to be analyzed can be identified by referring to a base sequence database (that is to say, which gene the DNA to be analyzed is can be determined).

The length of the probe is preferably 300 bases or shorter. It is preferably at least 8 base pairs, at least 9 base pairs, at least 10 base pairs, at least 11 base pairs, at least 12 base pairs, at least 13 base pairs, at least 14 base pairs, at least 15 base pairs, at least 16 base pairs, at least 17 base pairs, at least 18 base pairs, at least 19 base pairs or at least 20 base pairs. In addition, the length of the probe is, preferably, 100 base pairs or less, 80 base pairs or less, 60 base pairs or less, 50 base pairs or less, 40 base pairs or less, 35 base pairs or less, 30 base pairs or less, 25 base pairs or less, 24 base pairs or less, 23 base pairs or less, 22 base pairs or less, 21 base pairs or less, 20 base pairs or less, 19 base pairs or less, 18 base pairs or less, 17 base pairs or less, 16 base pairs or less, 15 base pairs or less, 14 base pairs or less, 13 base pairs or less, 12 base pairs or less, 11 base pairs or less or 10 base pairs or less.

The probe of the present invention can be synthesized according to well known methods such as chemical synthesis methods.

(Ligation by a DNA Ligase)

In Step (a), the DNA to be analyzed and a probe are ligated by a DNA ligase. When a DNA to be analyzed, probes and a DNA ligase are reacted, the DNA to be analyzed and the probe in which the base at the protruding end is complementary to the base at the protruding end of the DNA being the subject of the analysis (may be referred to as complementary probe) become ligated. The DNA ligase used suffices to be one capable of connecting DNA fragments having protruding ends, and is not limited in particular. As DNA ligases, for instance, T4 DNA ligase, Pfu DNA ligase, Taq DNA ligase, TTH DNA ligase and the like, can be included.

(2) Step (b): Identification of the Species of the Identification Label on the Probe Ligated to the DNA to be Analyzed Step (b) is a step in which the species of the identification label on the probe that has been ligated to the DNA to be analyzed in Step (a) is identified.

As described above, since the probes are labeled using a labeling substance distinguishable from one another for each species of the base protruding at the ends thereof (identification labeled), the species of the base at the protruding end of a probe can be identified by identifying the species of the identification label. In addition, since the base at the protruding end of the probe is complementary to the base at the protruding end of the DNA to be analyzed that has been ligated to the probe, the species of the base at the protruding end of the DNA to be analyzed that has been ligated to the probe can be identified by identifying the base at the protruding end of the probe. In this way, when the protruding ends of the DNA to be analyzed and the probe are 3' protruding ends, the base at the 3' end of the DNA to be analyzed becomes identified, and when the protruding ends of the DNA to be analyzed and the probe are 5' protruding ends, the base at the 5' end of the DNA to be analyzed becomes identified.

For the identification of the species of the identification label, a method is used, whereby a signal obtained according to the labeling substance used is detected, allowing the species of the labeling substance to be identified. As such identification method of species of identification labels, a method capable of distinguishing between a probe ligated to the DNA to be analyzed and a (free) probe not ligated to the DNA to be analyzed is preferred. As a method capable of distinguish between a probe ligated to the DNA to be analyzed and a (free) probe, for instance, a method by single molecule observation may be included. According to single molecule observation, since only the probes immobilized on a glass surface are detected as a bright spots, and free probes are detected as weak uniform background noise, respectively, ligated probes and free probes can be distinguished. Specifically, for instance, if the labeling label is a fluorescent label, for the identification of the species of the fluorescent label, a method is used, whereby the fluorescence wavelength of the fluorescent label is detected to identify the species of the fluorescent label, for instance, a spectrofluorimetric method. In addition, as a method capable of distinguishing between a probe ligated to the DNA to be analyzed and a free probe, for instance, the single molecule spectrofluorimetry method is used. Single molecule spectrofluorimetry can be carried out using, for instance, a single molecule fluorescence spectromicroscope, a commercially available single molecule fluorescence analysis system (for instance, MS20 (manufactured by Olympus) or the like), a spectral optical system using a prism or a diffraction grating, a system combining a plurality of CCD cameras and filters, a high-speed filter switching device, a 3CCD camera, a single-chip color CCD camera, a digital CCD camera (for instance, EM-CCD camera and the like), Quad-View™ (Roper Bioscience), Dual-View™ (Roper Bioscience), Dual-Cam™ (Roper Bioscience), Double-View, and the like. As single molecule spectrofluorimetry methods used in the present invention, for instance, Fluorescence Correlation Spectroscopy (for instance, refer to Biopolymers, 13, 29-61 (1974) or the like), Fluorescence Intensity Multiple Distribution Analysis (for instance, refer to Biophysical Journal, 79, 2858-2866 (2000), Published Patent Application No. 2001-502062, Published Patent Application No. 2001-518307, Published Patent Application No. 2002-505742 and the like) and the like, can be included.

As light sources used in the excitation of the fluorescent label, well known light sources can be used, such as, arc light sources such as mercury lamp and xenon lamp, and laser beam sources such as LED, Ar laser, HeNe laser, LD laser, HeCd laser, NdYAG laser and KrAr laser. The wavelength of the light source is selected according to the excitation wavelength of the fluorescent label being used. When a light source having a broad wavelength region such as an arc light source is used, a band pass filter is preferably used according to the excitation wavelength of the fluorescent label being used. As band pass filters, for instance, dielectric band pass filter, metal band pass filter and the like, can be included. A light source having a broad wavelength region such as an arc light source can be used preferably, on the point that an excitation light according to the fluorescent label can be selected readily by suitably selecting a band pass filter.

When detecting fluorescence, observing by lowering the background light is preferred, by separating fluorescence from lights other than fluorescence, such as excitation light and scattering light. Such separation between fluorescence and other lights (excitation light, scattering light and the like) is preferably carried out using a dichroic mirror, an absorption filter and the like. As dichroic mirror, it suffices to select one with wavelength characteristics such as reflecting excitation light and transmitting fluorescence, according to the excitation wavelength and fluorescence wavelength of the fluorescent label. As absorption filter, it suffices to select one that transmits fluorescence and absorbs scattering light or the like.

As a detector for detecting fluorescence of fluorescent label, for instance, a CCD camera may be included. From the point of view of noise reduction a cooled CCD camera is preferably used. When detecting fluorescence using a CCD camera, obtaining a spectrum of the fluorescence using a spectral separation element such as a prism is preferred for the identification of the fluorescent label.

An image obtained as above may be analyzed using commercially available image analysis software, for instance, MetaMorph (Universal Imaging Corporation) or the like.

(3) Step (c): Cleavage by a Restriction Enzyme of the Ligated DNA of the DNA to be Analyzed and the Probe Step (c) is a step in which the ligated DNA of the DNA to be analyzed and the probe, which has been ligated in Step (a), is cleaved by a restriction enzyme. As described above, since the distance between the recognition sequence and the protruding end of the probe is shorter than the distance between the recognition sequence and the cleavage site, a cleavage site appears on the DNA to be analyzed by the DNA to be analyzed and the probe becoming ligated. Specifically, for instance, when the protruding ends of the DNA to be analyzed and the probe are one base-protruding ends, since the distance between the recognition sequence and the protruding end of the probe is one base shorter than the distance between the recognition sequence and the cleavage site, if the DNA to be analyzed and the probe become ligated, a cleavage site appears between the first and the second bases from the terminus of the DNA to be analyzed. By this ligated DNA of the DNA to be analyzed and the probe being cleaved by the restriction enzyme, one base is deleted from the terminus of the DNA to be analyzed, generating a new one base-protruding end.

The restriction enzyme used in the present invention is a restriction enzyme whose recognition sequence is apart from the cleavage site, and is one that also generates a protruding end. The generated protruding end may be a 3' protruding end or may be a 5' protruding end. In addition, as the number of protruding bases, it is not is not limited in particular, and the generated protruding end is preferably a one or two base-protruding end, and in particular a one base-protruding end is preferred. Such a restriction enzyme is selected from, for instance, class IIS restriction enzymes. Specifically, for instance, as restriction enzymes generating a 3' protruding end with a one base protrusion, BmrI and isoschizomers thereof (for instance, BfiI, BmuI and the like), AsuHPI and isoschizomers thereof (for instance, HphI and the like), BciVI and isoschizomers thereof (for instance, BfuI and the like), HpyAV and isoschizomers thereof, MboII and isoschizomers thereof (for instance, NcuI and the like), MnlI and isoschizomers thereof and the like, can be included, among which BmrI, BciVI, MboII, HphI are preferred, and in particular BmrI is preferred. As restriction enzymes generating a 5' protruding end with a one base protrusion, AclWI and isoschizomers thereof (for instance, AlwI, BinI, BspPI, BstH9I, Bst31TI, EacI and the like), BccI and isoschizomers thereof (for instance, HpyC1I and the like), BcefI and isoschizomers thereof, PleI and isoschizomers thereof (for instance, PpsI and the like) and the like, can be included, among which AlwI, PleI, BcefI, HpyC1I are preferred, and in particular AlwI and PleI are preferred.

As restriction enzymes generating a 3' protruding end with a two base protrusion, for instance, AciI and isoschizomers thereof (for instance, SsiI and the like), BceAI and isoschizomers thereof, Bme5851 and isoschizomers thereof (for instance, BstFZ438I, FauI, SmuI and the like), BscAI and isoschizomers thereof (for instance, Bst19I and the like) and the like, can be included. As restriction enzymes generating a 5' protruding end with a two base protrusion, for instance, Asp26HI and isoschizomers thereof (for instance, Asp27HI, Asp35HI, Asp36HI, Asp40HI, Asp50HI, BmaHI, BsaMI, BscCI, BsmI, Mva1269I, PctI and the like), Bce83I and isoschizomers thereof (for instance, BpuEI and the like), BcgI and isoschizomers thereof, BpmI and isoschizomers thereof (for instance, GsuI and the like), Bse1I and isoschizomers thereof (for instance, BseNI, BsrI, BsrSI, Bst11I, Tsp1I and the like), Bse3DI and isoschizomers thereof (for instance, BseMI, BsrDI and the like), BseGI and isoschizomers thereof (for instance, BstF5I, BtsCI and the like), BsgI and isoschizomers thereof, BspKT5I and isoschizomers thereof, BtsI and isoschizomers thereof, CspCI and isoschizomers thereof, CstMI and isoschizomers thereof, EciI and isoschizomers thereof, Eco57MI and isoschizomers thereof, TspDTI and isoschizomers thereof, TspGWI and isoschizomers thereof and the like, can be included.

The restriction enzyme used in the present invention is selected according to the probe used in Step (a). Specifically, a restriction enzyme having a cleavage site that forms a protruding end having the same strand of protruding end (5' or 3') and number of bases in the protruding end as the protruding end of the probe used in Step (a) is used. Specifically, for instance, if the protruding end of the probe is a 3' protruding end with a one base protrusion, a restriction enzyme having a cleavage site generating a one base protrusion at the 3' end is used. If the protruding end of the probe is a 5' protruding end with a one base protrusion, a restriction enzyme having a cleavage site generating a one base protrusion at the 5' end is used. In addition, the restriction enzyme to be used is one in which the distance between the recognition sequence and the cleavage site is longer than the distance between the recognition sequence and the protruding end of the probe to be used by the number of bases determined at once in Step (b). Therefore, when the number of bases determined at once in Step (b) and the number of bases of the DNA protruding at the protruding end are equal, the distance between the recognition sequence and the cleavage site is one that is longer than the distance between the recognition sequence and the protruding end of the probe to be used by the number of bases of the DNA protruding at the protruding end. Specifically, for instance, since when the protruding end of the probe to be used is a one base-protruding end, the number of bases determined at once in Step (b) is also one base, a restriction enzyme for which the distance between the recognition sequence and the cleavage site is one base longer than the distance between the recognition sequence and the protruding end is used. In addition, for instance, when the protruding end is a two base-protruding end and the number of bases determined at once is two bases, a restriction enzyme for which the distance between the recognition sequence and the cleavage site is two bases longer than the distance between the recognition sequence and the protruding end is used. Conversely, when determining a sequence, one base at a time, using probes having two base-protruding ends, for instance, NA, NT, NG and NC, even if the protruding end is a two base-protruding end, a restriction enzyme for which the recognition sequence and the cleavage site are one base longer than the distance of the distance between the recognition sequence and the protruding end is used. In addition, when analyzing bases, two bases or more at a time, using probes having protruding ends of two bases or more, such as when analyzing the bases in the DNA to be analyzed, two bases at a time, using probes having two base-protruding ends, NA, NT, NG and NC, a restriction enzyme for which the distance between the recognition sequence and the cleavage site is two bases or more longer than the distance between the recognition sequence and the protruding end is used.

(4) Determination of the Base Sequence of the DNA to be Analyzed

As described above, the DNA to be analyzed is ligated to the probe in Step (a) and the base at the protruding end of the DNA to be analyzed is identified in Step (b). Then, in Step (c), a new protruding end is generated on the DNA to be analyzed. In this way, the DNA to be analyzed with a new protruding end generated can be further subjected to Steps (a) to (c), reiterating Steps (a) to (c) in a similar manner. This reiteration of Steps (a) to (c) can be carried out as long as cleavage by the restriction enzyme in Step (c) is possible. Through such reiteration of Steps (a) to (c), the base sequence of the DNA to be analyzed can be determined (or analyzed) by sequentially identifying the base at the protruding end of the DNA to be analyzed. Specifically, if the protruding end of the DNA to be analyzed is a 3' protruding end, the base sequence of the DNA to be analyzed can be sequentially determined (or analyzed) from the 3' side. If the protruding end of the DNA to be analyzed is a 5' protruding end, the base sequence of the DNA to be analyzed can be sequentially determined from the 5' side. In addition, if the protruding end of the DNA to be analyzed is a one base-protruding end, determination is possible one base at a time.

Such reiteration of Steps (a) to (c), (1) can be carried out by exchanging the reaction solution after one or two reactions of Step (a), Step (b) and Step (c) have been carried out, or (2) can also be carried out by chain reaction under the co-presence of the DNA to be analyzed, probes, DNA ligase and restriction enzyme. The reiteration of Steps (a) to (c) is preferably carried out with a chain reaction from the point of view of analysis speed.

As mentioned in (1) above, when it is to be carried out by exchanging the reaction solution after one or two reactions of Step (a), Step (b) and Step (c) have been carried out, for instance, it can be carried out by a method in which the reaction solution is exchanged by a pump, or the like, in a system combining a microflow path and a temperature regulation device. Since the DNA ligation reaction and the DNA cleavage reaction differ in their optimal reaction conditions, each reaction may be carried out by alternately changing the reaction conditions to be in the optimal conditions of the respective reactions.

In the following, one embodiment of the base sequence determination method for DNA of the present invention will be described Specifically based on FIG. 1 and FIG. 2.

First, one embodiment of Step (a) will be described. As shown in FIG. 1 (1), the DNA to be analyzed is immobilized to a support indirectly via avidin/biotin conjugation at the terminus opposite to the protruding end. The strand on the upper side of the DNA to be analyzed has 5' end on the left and 3' end on the right. Consequently, the protruding end of the DNA to be analyzed is a one base-protruding 3' end. The bases of the DNA to be analyzed are represented in order from the base at the 3' protruding end, as the first base, the second base and the third base.

The probe is labeled at the terminus opposite to the protruding end using a fluorescent substance distinguishable from one another for the species of the base at the protruding end. Specifically, Probe 1, which base at the protruding end is T, is labeled with Fluorescent Substance 1 (FL 1). Similarly, Probes 2, 3 and 4, which bases at the protruding ends are respectively A, C and G, are labeled respectively with Fluorescent Substances 2, 3 and 4 (FL 2, 3 and 4). The strands on the lower side of Probes 1 to 4 have 3' ends on the left and the 5' end on the right. Consequently, the protruding ends of the probes are one base-protruding 3' ends, similarly to the DNA to be analyzed. The probes contain a recognition sequence for the BmrI restriction enzyme. The distance between the recognition sequence and the protruding end is one base shorter than the distance between the recognition sequence and the cleavage site for the BmrI restriction enzyme.

Since the base (the first base) at the protruding end of the DNA to be analyzed is A, Probe 1 having T at the protruding end, which is complementary thereto, becomes ligated by the DNA ligase, generating a ligated DNA as shown in FIG. 1 (2).

In the following, one embodiment of Step (b) will be described. By analyzing, using a spectrofluorimetry method, or the like, the ligated DNA generated in Step (a) between the DNA to be analyzed and Probe 1 (FIG. 1 (2)), the fluorescent label (Fluorescent Substance 1) on the probe that has been ligated to the DNA to be analyzed is identified. A spectrofluorimetric device, for instance, such as shown in FIG. 2 (1), is used for the identification of such a fluorescent label. In the spectrofluorimetric device of FIG. 2 (1), a light at the wavelength required to excite the fluorescent substance is extracted with a band pass filter, from a light emitted from a light source. The excitation light extracted in this way is reflected by a dichroic mirror and irradiates the sample. The fluorescent label on probe becomes excited by the irradiated excitation light, and emits fluorescence. The fluorescence emitted from the fluorescent label is transmitted through the dichroic mirror, spectrally separated by a prism, and then observed by a cooled CCD. Note that in general, single molecule spectrofluorimetry is carried out by combining the use of a magnifying optical system such as a fluorescence microscope. According to the single molecule spectrofluorimetry method, from the magnitude of fluctuation, or the like, the probes ligated to the DNA to be analyzed and the free probes can be distinguished, such that the use of single molecule spectrofluorimetry method is preferred. In this way, for instance, the probe ligated to the DNA to be analyzed shown in FIG. 1 (2) is identified to be Probe 1. In addition, the base at the protruding end of the DNA to be analyzed is identified to be a base (A) complementary to the base (T) at the protruding end of Probe 1.

As sample, for instance, as shown in FIG. 2 (2), one in which a plurality of DNAs to be analyzed have been immobilized on a support can also be used. According to the single molecule spectrofluorimetry method, simultaneous observations of a multitude (for instance, several hundreds to several thousands) of fluorescence is also possible, such that by using a sample in which a plurality of DNAs to be analyzed have been immobilized on a support, simultaneous determinations of a plurality (for instance, several hundreds to several thousands) of base sequences of the DNAs to be analyzed is also possible.

In the following, one embodiment of Step (c) will be described. As described above, since the distance between the recognition sequence and the protruding end on the probe is one base shorter than the distance between the recognition sequence and the cleavage site, by the DNA to be analyzed and the probe being ligated, a cleavage site has appeared between the first base and the second base of the DNA to be analyzed (FIG. 1 (2)). Consequently, when this ligated DNA of the DNA to be analyzed and the Probe I cleaved with a BrmI restriction enzyme, the first base of the DNA to be analyzed is cleaved while being in a ligated state to Probe 1, the DNA to be analyzed becomes cleaved one base shorter. As a result, a new one base-protruding end in which the second base is protruding is generated on the DNA to be analyzed (FIG. 1 (3)).

The DNA to be analyzed having a new one base-protruding end (second base (C)) generated in this way can be subjected further to Steps (a) to (c). That is to say, the DNA to be analyzed in which the second base (C) is protruding is ligated with Probe 4 having G at the protruding end, which is complementary thereto, by a DNA ligase (Step (a)). Hereafter, Step (b) and Step (c) can be carried out as described above, and furthermore, Steps (a) to (c) can be reiterated in a similar manner. Such reiteration of Steps (a) to (c) can be carried out as long as cleavage by the restriction enzyme in Step (c) is possible. Through such reiteration of Steps (a) to (c), the base sequence of the DNA to be analyzed is determined sequentially from the 3' side, one base at a time.

2. Probes and Base Sequence Determination Kit for DNA

In addition, another mode of the present invention relates to a probe, which is a probe having a protruding end and identification-labeled according to the species of the base at the protruding end, containing a recognition sequence for a restriction enzyme in which the recognition sequence and the cleavage site are apart, and a base sequence determination kit for DNA containing the probe.

As probes of the present invention, similar ones to those described earlier may be included, and similar ones to those described earlier are preferred. For instance, those with a 3' protruding end and those with a 5' protruding end for the protruding end may be included. Among them, those in which the protruding end is a one-base-protruding end are preferred. In addition, those in which the distance between the recognition sequence and the one-base-protruding end is one base shorter than the distance between the recognition sequence and the base cleavage site are preferred. In addition, those in which the recognition sequence is a recognition sequence for a class IIS restriction enzyme is preferred.

The base sequence determination kit for DNA of the present invention is used to determine the base sequence of a DNA by methods containing the above Step (a) to Step (c). As probes included in the kit of the present invention, the probes of the present invention described earlier may be included, and similar ones to those described earlier are preferred. In particular, a kit containing as probes at least four species of probe having one base-protruding ends that are complementary to respectively A, T, C or G, is preferred.

The kit of the present invention may further contain a restriction enzyme. As restriction enzymes included in the kit of the present invention, the restriction enzymes used in the above Step (c) and restriction enzymes for forming a protruding end on the DNA to be analyzed may be included. As such restriction enzymes, similar ones to those described earlier may be included, and similar ones to those described earlier are preferred.

The kit of the present invention may further contain a DNA ligase. As DNA ligases, similar ones to those described earlier may be included, and similar ones to those described earlier are preferred.

3. Base Sequence Determination Device for DNA

In addition, another mode of the present invention is a device, which is a base sequence determination device for DNA provided with (i) a measurement cell, (ii) optical means, (iii) means for converting optical information into an identification signal, and (iv) means for converting the identification signal into base sequence information, the measurement cell being provided with (a) means for ligating a DNA to be analyzed, wherein said DNA has a protruding end and is immobilized on a support, and a probe by a DNA ligase, wherein said probe has a protruding end and identification-label according to the species of the base at the protruding end, and said probe contains a recognition sequence of a restriction enzyme whose recognition sequence is apart from the cleavage site; and (c) means for cleaving the ligated DNA of the DNA to be analyzed and the probe by a restriction enzyme whose recognition sequence is apart from the cleavage site.

In the base sequence determination device for DNA of the present invention, first, in the (i) measurement cell (a) a reaction is carried out to ligate a DNA to be analyzed, wherein said DNA has a protruding end and is immobilized on a support, and a probe by a DNA ligase, wherein said probe has a protruding end and identification-label according to the species of the base at the protruding end, and said probe contains a recognition sequence of a restriction enzyme whose recognition sequence is apart from the cleavage site. Next, by way of (ii) optical means, optical information (for instance, color information) is obtained from the identification label of the probe that has been ligated to the DNA to be analyzed. By way of (iii) means for converting optical information into an identification signal, the obtained optical information is converted into an identification signal (for instance, electrical signal) that may identify the identification label on the probe. By way of (iv) means for converting the identification signal into base sequence information, a base sequence is obtained. Thereafter, in the (i) measurement cell (c) a reaction is carried out to cleave the ligated DNA of the DNA to be analyzed and the probe by a restriction enzyme whose recognition sequence is apart from the cleavage site. Thereafter, by repeating further the above steps, the base sequence of the DNA to be analyzed can be determined sequentially. Note that the above each step can be carried out by way of the base sequence determination method for DNA of the present invention described earlier.

Hereafter, each constitutive element will be described.

(i) Measurement Cell

The measurement cell is provided with an inlet to let in the support where the DNA to be analyzed has been immobilized, probes, buffer, restriction enzyme and the like, and an elimination port to eliminate these. Here, there is no necessity to install an inlet and an elimination port separately, and an in-and-out port to carry out feeding and elimination may also be installed. When a fluorescent substance, a quantum dot, a metal colloid, and the like, are used for the identification label on the probe, the material of the measurement cell is preferably a material having transparency to light, and in addition, glass, quartz glass, silicon, single crystal transparent to light (for instance, $Al_2O_3$, $SiO_2$) and the like, are preferred. The measurement cell per se may also be used as a support for immobilizing the DNA to be analyzed.

(ii) Optical Means

The optical means is constituted by an optical system, or the like, capable of obtaining optical information (for instance, color information) that may identify the identification label on the probe. Specifically, for instance, as an optical system used when the labeling label is a fluorescent label or a quantum dot, for instance, a fluorescence microscope, or the like, preferably, a single molecule fluorescence spectromicroscope, or the like, can be included. Optical means used in the present invention may be provided with a spectral optical system using a prism or a diffraction grating, high-speed filter switching device, and the like.

(iii) Means for Converting Optical Information into an Identification Signal

Means for converting optical information (for instance, color information or the like) into an identification signal (for instance, electrical signal or the like), is means for converting optical information that may indentify the identification label on the probe obtained by way of the above (ii) optical means, into an identification signal (for instance, electrical signal or the like) that may identify the identification label on the probe. As means for converting optical information into an identification signal, means may be included, for instance, whereby optical information that may identify the identification label on the probe is separated spectrally, then imaged onto different pixels on different CCDs or on one CCD, and based on the brightness information from the pixels present in the imaged portion, converted into an identification signal (for instance, electrical signal or the like) that may identify the identification label on the probe. Note that, as CCD, in general, a digital CCD is used. When a digital CCD is used, the identification signal can be obtained as a digital signal. As a digital signal is suitable for processing by a computer, it is desirable in automating the following (iv) means for converting the identification signal into base sequence information using a computer. In addition, when the optical information, after spectral separation, is converted into a brightness signal using different CCDs, the brightness information from each CCD chip can be distinguished, such that the species of identification label on the probe can be identified from the obtained identification signal readily on a computer. Therefore, using different CCDs (for instance, 3CCD) for means for converting optical information into an identification signal is preferred, since the following
(iv) Means for Converting into Base Sequence Information can be Automated Readily.

In addition, conversion of optical information into identification information is preferably carried out by a unit of one molecule.
(iv) Means for Converting an Identification Signal into Base Sequence Information Means for converting the identification signal into base sequence information is means for converting into base sequence information of DNA an identification signal (for instance, electrical signal or the like) obtained by way of the above (iii) means for converting optical information into an identification signal.

As described above, since each probe has been applied a label distinguishable from one another (identification labeled) for each the species of the base at the protruding end thereof, the species of the base at the protruding end of the probe can be identified by identifying the species of identification label. In addition, since the base at the protruding end of the probe is complementary to the base at the protruding end of the DNA to be analyzed that has been ligated to the probe, the species of the base at the protruding end of the DNA to be analyzed that has been ligated to the probe can be identified by identifying the base at the protruding end of the probe. Then, since the identification signal corresponding to each identification label on the probe can be obtained by way of (iii) described above, the species of the base at the protruding end of the DNA to be analyzed can be identified from the identification signal obtained in (iii) described above. Here, since the identification signal obtained in (iii) described above can be obtained as an electric signal that may be processed by a computer provided with generally used constitutive elements (for instance, a memorization unit such as a RAM, a ROM and a hard disk, a program stored in a memorization unit, an input unit such as a keyboard and a computational unit such as a CPU), means for converting the identification signal into base sequence information can be automated readily. The base sequence information converted by way of a computer can be displayed or sent out by way of a display unit such as a monitor or an output unit such as a printer.

The SEQ ID Nos. of the present description indicate the following sequences.

[SEQ ID No.: 1] Shows the base sequence of one strand of Probe 1.
[SEQ ID No.: 2] Shows the base sequence of the other strand of Probe 1.
[SEQ ID No.: 3] Shows the base sequence of one strand of Probe 2.
[SEQ ID No.: 4] Shows the base sequence of the other strand of Probe 2.
[SEQ ID No.: 5] Shows the base sequence of one strand of Probe 3.
[SEQ ID No.: 6] Shows the base sequence of the other strand of Probe 3.
[SEQ ID No.: 7] Shows the base sequence of one strand of Probe 4.
[SEQ ID No.: 8] Shows the base sequence of the other strand of Probe 4.
[SEQ ID No.: 9] Shows the base sequence of one strand of the DNA to be analyzed used in Example 1.
[SEQ ID No.: 10] Shows the base sequence of the other strand of the DNA to be analyzed used in Example 1.
[SEQ ID No.: 11] Shows the base sequence of one strand of the quantum dot 525-DNA probe used in Example 2.
[SEQ ID No.: 12] Shows the base sequence of the other strand of the quantum dot 525-DNA probe used in Example 2.
[SEQ ID No.: 13] Shows the base sequence of one strand of the quantum dot 605-DNA probe used in Example 2.
[SEQ ID No.: 14] Shows the base sequence of the other strand of the quantum dot 605-DNA probe used in Example 2.
[SEQ ID No.: 15] Shows the base sequence of one strand of the DNA to be analyzed used in Example 2.
[SEQ ID No.: 16] Shows the base sequence of the other strand of the DNA to be analyzed used in Example 2.
[SEQ ID No.: 17] Shows the base sequence of one strand of the quantum dot (525) probe used in Example 3.
[SEQ ID No.: 18] Shows the base sequence of the other strand of the quantum dot (525) probe used in Example 3.
[SEQ ID No.: 19] Shows the base sequence of one strand of the quantum dot (565) probe used in Example 3.
[SEQ ID No.: 20] Shows the base sequence of the other strand of the quantum dot (565) probe used in Example 3.
[SEQ ID No.: 21] Shows the base sequence of one strand of the quantum dot (605) probe used in Example 3.
[SEQ ID No.: 22] Shows the base sequence of the other strand of the quantum dot (605) probe used in Example 3.
[SEQ ID No.: 23] Shows the base sequence of one strand of the quantum dot (655) probe used in Example 3.
[SEQ ID No.: 24] Shows the base sequence of the other strand of the quantum dot (655) probe used in Example 3.

Unless there is a particular mention in the present description (including the following examples) regarding cloning and other manipulations, reaction conditions and the like, it can be carried out by methods described in standard protocol compilations, such as, Sambrook J. et al., Molecular Cloning: A Laboratory Manual, Third Edition, Cold Spring Harbor Laboratory Press (2001) (hereinafter, may sometimes be abbreviated as Molecular Cloning, 3rd Edition); Ausbel F. M. et al., Current Protocols in Molecular Biology, Supplement 1 to 38, John Wiley and Sons (1987-1997); and Glover D. M. and Hames B. D., DNA Cloning 1: Core Techniques, A practical Approach, Second Edition, Oxford University Press (1995), or methods according thereto.

EXAMPLES

Hereinafter, the present invention will be described more specifically based on examples. Note that the present invention is not limited to these examples.

Example 1

Incorporation of a Sequence-Specific Fluorescent Probe in a Multimolecular System The base sequence of a DNA was determined by detecting a fluorescent DNA probe that binds specifically to the sequence of a DNA having a one base-protruding end and further reacting alternately a Class IIS restriction enzyme and a DNA ligase.
(1) Immobilization of DNA to be Analyzed onto a Support
Biotinylated DNA comprising biotin conjugated to the DNA to be analyzed (FIG. 3) (SEQ ID No.: 9: 5' biotin-GCTACGTAAGCTTCATGAATTCGACACTGTGTCAG-CA 3', SEQ ID No.: 10: 5' GCTGACACAGTGTCGAAT- TCATGAAGCTTACGTAGC 3') (10 μM) was mixed with avidin-agarose beads (Sigma, A9207) (suspended with 1×PBS into a 30 μl slurry) and admixed for one hour to immobilize the DNA to be analyzed onto avidin-agarose beads.

(2) Ligation of the DNA to be Analyzed and Fluorescent DNA Probes

Beads having the DNA to be analyzed obtained immobilized in (1) above were washed twice with 1×PBS, further washed once with a T4 DNA ligase buffer (50 mM Tris-HCl, 10 mM $MgCl_2$, 10 mM DTT), then, fluorescent DNA probes (10 μM, 50 mM Tris-HCl, 10 mM $MgCl_2$, mM DTT) (10 μl) and T4 DNA ligase (Toyobo, Ligation high, LGK-101) (10 μl) were mixed with the above agarose beads, incubated at 20° C. for one hour, washed twice with 1×PBS to connect the DNA to be analyzed and the fluorescent DNA probes.

Note that for the fluorescent DNA probes, ones with the same structure as Probe 1, 3 and 4 shown in FIG. 1 (1) were used. FITC as Fluorescent Substance 1 (FL 1), Cy5 as Fluorescent Substance 3 (FL 3) and Cy3 as Fluorescent Substance 4 (FL 4) were used.

(3) Identification of Fluorescent DNA Probe Ligated to the DNA to be Analyzed A portion of the beads connected with the fluorescent DNA probe obtained in (2) above was observed with a fluorescence microscope (Zeiss Axiovert 200M) to identify the fluorescent DNA probe connected on the beads surface.

(4) Cleavage of the Ligated DNA of the DNA to be Analyzed and the Fluorescent DNA Probe The beads identified with the fluorescent DNA probe in (3) above were washed once with 1× NEBuffer 2 (NEB, B7002S), then, BmrI (NEB, R0600S) (2 μt) and 1×NEBuffer 2 were added to the beads incubated at 37° C. for one hour incubate to cleave the ligated body of the DNA to be analyzed and the fluorescent DNA probe.

Thereafter, washing was carried out twice with 1×PBS.

(5) Sequential Identification of DNA Base Sequence

DNA base sequence was sequentially identified by repeating (2) to (4) described above.

(6) Results

Figures 4, 5:
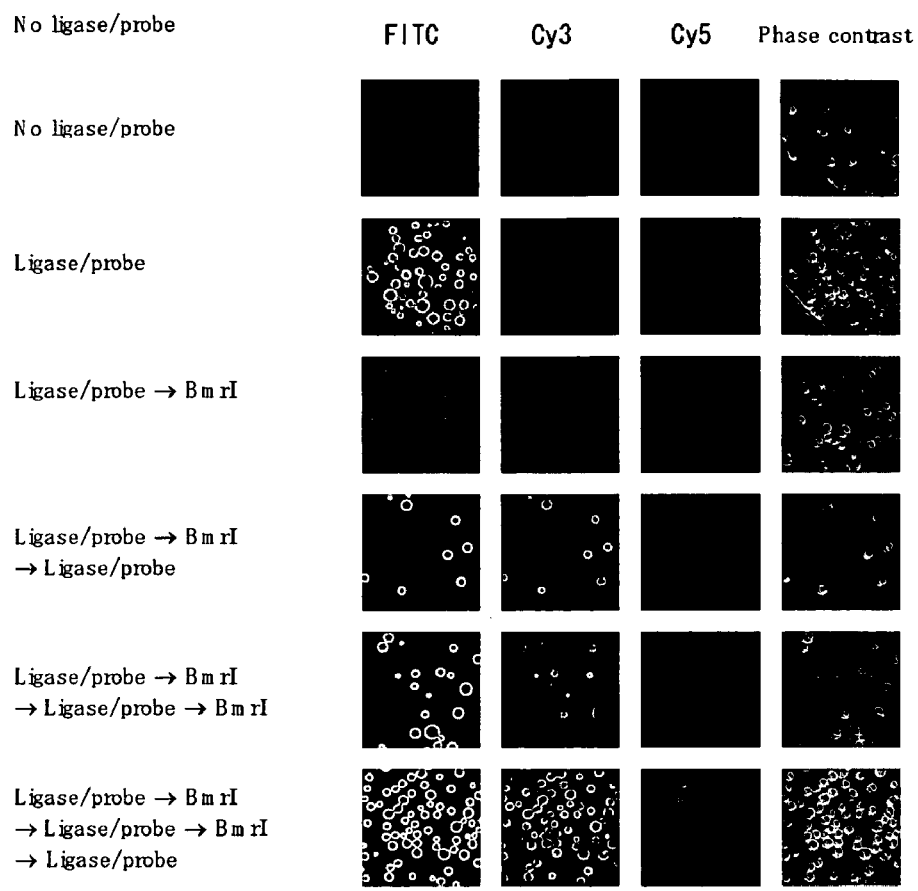
FIG. 4 is a figure showing the result of observation of beads to which the DNA to be analyzed of Example 1 was conjugated.
FIG. 5 is a figure showing the structures of the quantum dot DNA probes and the biotinylated DNA comprising the DNA to be analyzed conjugated with biotin, used in Example 2.

First, by carrying out (1) to (3), fluorescence of FITC was observed, and the first base of the 3' end of the DNA to be analyzed was identified to be A. Next, by carrying out (4) and (2) to (3) repeatedly, fluorescence of Cy3 was observed, and the second base of the 3' end of the DNA to be analyzed was identified to be C. In addition, by carrying out (4) and (2) to (3) repeatedly, fluorescence of Cy5 was observed, and the second base of the 3' end of the DNA to be analyzed was identified to be G. In this way, three bases of the base sequence of the DNA to be analyzed were identified by the fluorescence wavelengths of the connected fluorescent probes (FIG. 4).

Note that, in the second round of base identification, the fluorescence of FITC was observed along with the fluorescence of Cy3, as shown in FIG. 3. This indicates that a portion of the plurality of (on the order of 100) DNAs to be analyzed bound to the avidin-agarose beads proceeded to the next reaction without undergoing cleavage by BmrI. Similarly, in the third round of base identification, the fluorescence of FITC and Cy3 were observed along with the fluorescence of Cy5; this indicates that a portion of the DNA to be analyzed proceeded to the next reaction without undergoing cleavage by BmrI in the first round or the second round. Thus, since there is the possibility that, when a plurality of DNAs to be analyzed is processed simultaneously, a portion thereof, proceeds to the following reaction while still unreacted, it is desirable to carry out the identification of an identification label by single molecule observation.

Example 2

A combination of base sequences of DNA was analyzed by single molecule observation of a chain reaction by a restriction enzyme and a ligase.

(1) Preparation of Quantum Dot-DNA Probes

Using a crosslinking agent (EDC), quantum dots (525 and 605) (Q21341MP Qdot (registered trade mark) 525 ITK™ Carboxyl Quantum Dots, and Q21301MP Qdot (registered trade mark) 605 ITK™ Carboxyl Quantum Dots, Invitrogen Corporation) were respectively bound covalently to the amino groups at 5' of the DNAs described below to prepare quantum dot-DNA probes.

```
Quantum dot 525 (FIG. 5 (1a)):
SEQ ID No.: 11: 5' cgtcccagtactagtatgc 3'

SEQ ID No.: 12: 5' amine-gcatactagtactgggacgc 3'

Quantum dot 605 (FIG. 5 (1b)):
SEQ ID No.: 13: 5' cgtcccagtactagtatgc 3'

SEQ ID No.: 14: 5' amine-gcatactagtactgggacgt 3'
```

(2) Immobilization of the DNAs to be Analyzed onto a Support

First, avidin (Sigma, A9275) was immobilized on the surface of a cover glass. Biotinylated DNA comprising biotin bonded to the DNA to be analyzed (FIG. 5 (2)), (SEQ ID No.: 15: 5' biotin-actcggcatgcgccagagagagagagagag 3' and SEQ ID No.: 16: 5' tctctctctctctctggcgcatgccgagt 3') (100 μM) was added to the cover glass with immobilized avidin and let to stand for one hour to immobilize the DNA to be analyzed onto the cover glass.

(3) Observation of Quantum Dot-DNA Probe Ligated to the DNA to be Analyzed

Figure 6:
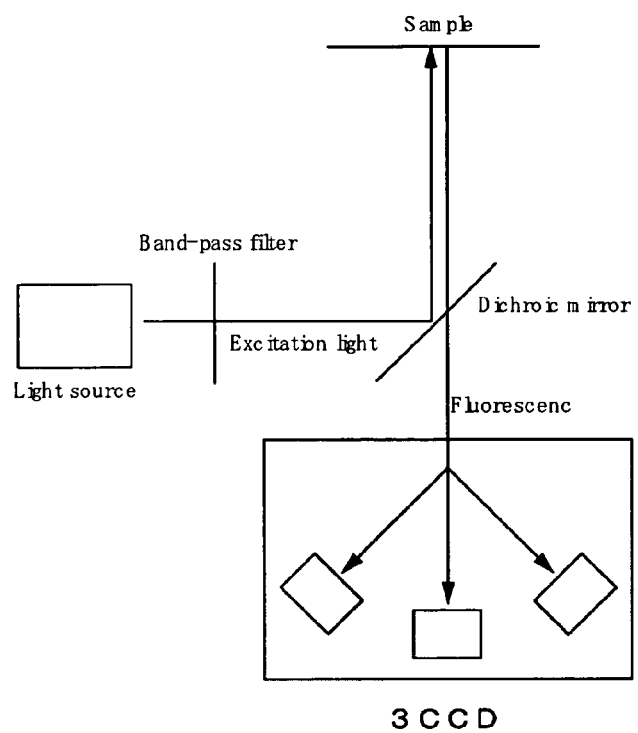
FIG. 6 is a figure showing an observation device for the quantum dot DNA probe in Example 2 and the observation results.
Figure 6:
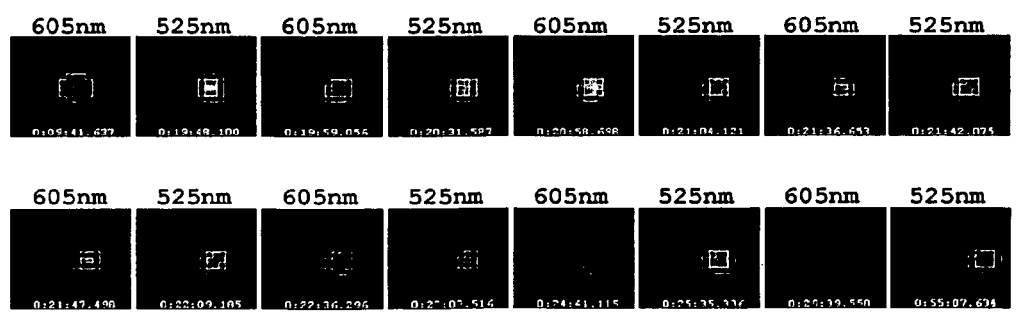

After the cover glass with immobilized DNA to be analyzed was washed with PBS, DNA probes conjugated with quantum dots (quantum dot-DNA probes), T4 DNA ligase (2 μl, NEB (New England Biolabs Inc.), M0202M), BmrI (5 μl, NEB, R0600L), ATP (1 mM), NEBuffer 2 (NEB) were placed over the surface of the cover glass, and the probes conjugating by chain reaction to the DNA to be analyzed were observed with a single molecule fluorescence microscope (Nikon TE2000 E, Plan Apo TIRF 100× NA1.45) and a 3CCD (Hamamatsu Photonics, C7780-20) (FIG. 6 (1)).

(4) Result

A chain of incorporations of quantum dot-DNA probes according to the base sequence of DNA to be analyzed was observed at a single molecule level (FIG. 6 (2)).

Example 3

The base sequence of a DNA was identified by way of single molecule observation of a chain reaction by a restriction enzyme and a ligase, using a support with a plurality of DNAs to be analyzed immobilized.

(1) Phosphorylation of Oligo DNA

Added with 22 μl of 10× T4 polynucleotide kinase buffer (NEB), 5 μl of ATP (100 mM) and 10 μl of T4 polynucleotide kinase (NEB), 200 µl of oligo DNA (50 µmol/µl) (Hokkaido System Science) was incubated at 37° C. for five hours. After incubation, phenol extraction (phenol: chloroform=1:1, stirring with a Vortex mixer for 10 seconds), chloroform wash (stirring with a Vortex mixer for 10 seconds), isopropanol precipitation (treatment for one minute with 50% isopropanol and 0.3M acetic acid sodium at room temperature, then centrifugation at 20000×g for 15 minute at 4° C.), and 70% ethanol wash (treatment with 1000 µl, then, centrifugation at 20000×g; number of washes: once) were carried out. After washing, [the oligo DNA] was dissolved in 10 mM Hepes-KOH (pH7.5) and annealed with the complementary strand.

(2) Preparation of Biotinylated DNA Substrate (DNA to be Analyzed)

The biotinylated DNA substrate (DNA to be analyzed) was received from Hokkaido System Science (HPLC purified product). The biotinylated DNA substrate (DNA to be analyzed) has a base sequence containing a base sequence comprising two or more (approximately ten to approximately 10,000) base sequences selected from the base sequences comprising, "tcaa", "tcat", "tcag" and "tcac", which have been ligated. The biotinylated DNA substrate was also phosphorylated by similar methods to (1) described above. Note that the length of the DNA to be analyzed is in general, on the order of 10 bp minimum and on the order of 10,000 bp maximum, on the order of 1,000 bp extent being particularly preferred.

(3) Preparation of Quantum Dot-DNA Probes

Using a crosslinking agent (EDC) in the following way, carboxyl group-added quantum dots (525, 565, 605 and 655) were covalently bonded to the amino groups at 5' of the respective oligo DNA probes described below to prepare quantum dot-DNA probes.

(Crosslinking Reaction and Purification)

Mixed with 1.5 µl of EDC (10 mg/ml), 30.5t of carbonate buffer (pH8.5, 0.1 M) and 48 µl of each oligo DNA probe (50 µmol/µl), 20 µl of each carboxyl group-added quantum dot (8 µM) was incubated at room temperature for three hours and covalently bonded to the amino group at 5' of each DNA to prepare quantum dot-DNA probes. The obtained quantum dot-DNA probes were solvent-exchanged to 10 mM Hepes-KOH pH 7.5 by way of gel filtration (NAP5, Amersham-Pharmacia).

(4) Immobilization of the DNA to be Analyzed onto a Glass Surface

A cover glass was ultrasonically washed with a strong alkaline washing agent (Scat 20×, Daiichi Clean Chemical), then washed with methanol and air dried. After drying, the cover glass was treated with a hydrophilic linker that has been conjugated with biotin, to coat the glass surface. On the surface of a cover glass coated with biotin (immobilization glass), 20 ng/ml of avidin (Avidin, Sigma) was applied, treated for 15 minutes, and then washed with Hepes-KOH. After washing, the biotinylated DNA substrate (DNA to be analyzed) prepared in (2) was applied, processed for 15 minutes, and then washed with Hepes-KOH.

(5) Observation of Quantum Dot-DNA Probes Ligated to the DNA to be Analyzed

After the cover glass with the immobilized DNA to be analyzed obtained in (4) described above was washed with PBS, the quantum dot-DNA probes obtained in (3) described above, T4 DNA ligase (2 µl, NEB, M0202M), ATP (100 mM), 10× reaction buffer (NEBuffer 2, NEB), Class IIS restriction enzyme (NEB, FokI) and ultra-pure water were placed over the surface of the cover glass, the quantum dot-DNA probes bonded by a chain reaction to the DNA to be analyzed were

```
(Oligo DNA probes conjugated to each carboxyl group-added
quantum dot)

Quantum dot 525:
(Q21341MP Qdot (registered trade mark) 525 ITK # Carboxyl
Quantum Dots, Invitrogen Corporation)
SEQ ID No.: 17:
5' amine-tgcctgacatgtgtacgtctcgattagcacgaagtcaggatgcagtg 3'

SEQ ID No.: 18:
5' agttcactgcatcctgacttcgtgctaatcgagacgtacacatgtcagga 3'

Quantum dot 565:
(Q21331MP Qdot (registered trade mark) 565 ITK # Carboxyl
Quantum Dots, Invitrogen Corporation)
SEQ ID No.: 19:
5' amine-tgcctgacatgtgtacgtctcgattagcacgaagtcaggatgcagtg 3'

SEQ ID No.: 20:
5' agtacactgcatcctgacttcgtgctaatcgagacgtacacatgtcagga 3'

Quantum dot 605:
(Q21301MP Qdot (registered trade mark) 605 ITK # Carboxyl
Quantum Dots, Invitrogen Corporation)
SEQ ID No.: 21:
5' amine-tgcctgacatgtgtacgtctcgattagcacgaagtcaggatgcagtg 3'

SEQ ID No.: 22:
5' agtccactgcatcctgacttcgtgctaatcgagacgtacacatgtcagga 3'

Quantum dot 665:
(Q21321MP Qdot (registered trade mark) 665 ITK # Carboxyl
Quantum Dots, Invitrogen Corporation)
SEQ ID No.: 23:
5' amine-tgcctgacatgtgtacgtctcgattagcacgaagtcaggatgcagtg 3'5'

SEQ ID No.: 24:
5' agtgcactgcatcctgacttcgtgctaatcgagacgtacacatgtcagga 3'
``` observed with an inverted-type fluorescence microscope (Nikon TE2000E) and an EM-CCD camera (Roper CascadeII) (refer to FIG. 6 (1)). The optical system and image analysis software used in the observation of the quantum dot-DNA probes were as follows:
(Optical System and Image Analysis Software)
  Inverted-type fluorescence microscope (Nikon TE2000E)
  Objective lens APO TIRF, oil immersion, 100× NA1.49
  Total reflection white illumination device
  High-speed filter changer (Prior)
  EM-CCD camera (Roper CascadeII)
  Dichroic mirror 505 nm
  Excitation filter 450 to 490 nm
  Fluorescence filter 520/10, 560/15, 605/20, 655/20
  Image analysis software MetaMorph (Universal Imaging Corporation)

Figure 7:
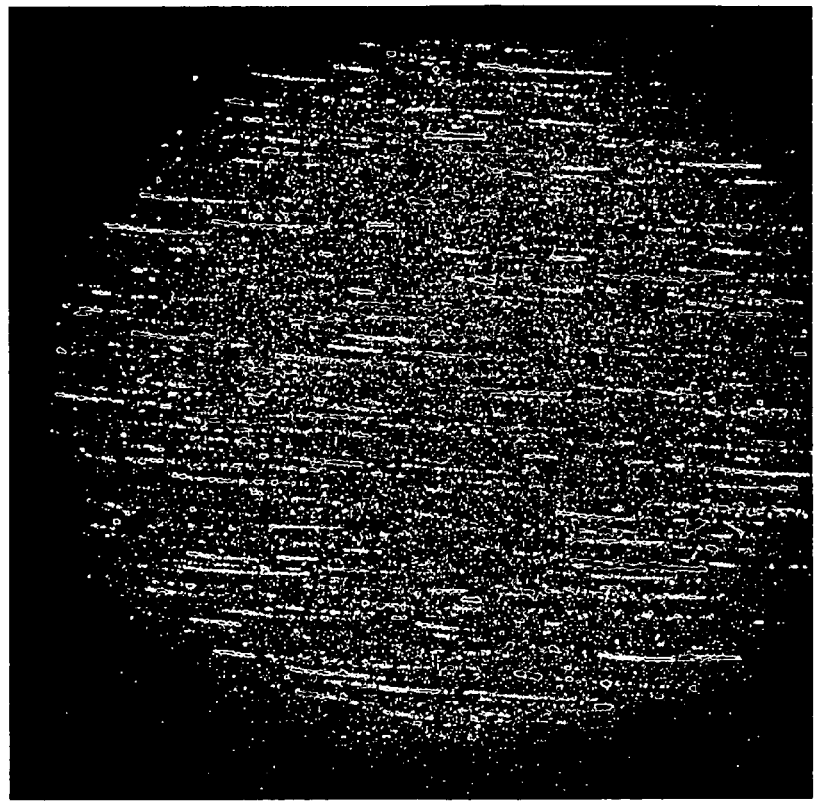
FIG. 7 is a figure showing the result of observation of the quantum dot probe conjugated to the DNA to be analyzed in Example 3. (2) is an image showing an enlargement of a portion of (1). (3) is a figure showing images at the same location in (2) arranged in a continuous sequence.
Figure 7:
Figure 7:
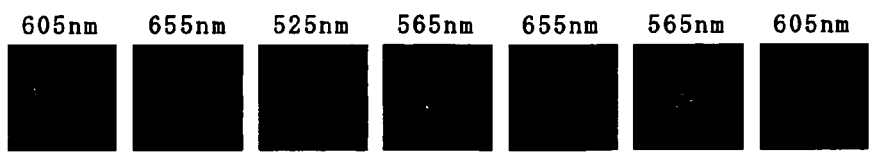

The reaction was observed under the conditions described above, and the result of overlapping the color changes against the time axis while shifting in the horizontal axis is shown in FIG. 7 (1). One line derives from the fluorescence of quantum dot-DNA probe bonded to one molecule of DNA, the left end of a line representing time zero.

An image of a magnified portion of FIG. 7 (1) is shown in FIG. 7 (2). How different wavelengths of the fluorescence were sequentially taken up according to the species of quantum dot-DNA probe bonded to the DNA to be analyzed was observed.

Images comprising an arrangement of a continuous sequence at an identical position of FIG. 7 (2) are shown in FIG. 7 (3). A chain of incorporations of quantum dot-DNA probes according to the base sequence of the DNA to be analyzed was observed at a single molecule level.

INDUSTRIAL APPLICABILITY

Since the base sequence determination method for DNA of the present invention has characteristics such as the base sequence of DNA can be determined effectively and the DNA extracted from cells can be observed directly without cloning, it is useful as a base sequence determination method for DNA, and in particular, a base sequence determination method for genomic DNA. In addition, since it can be realized with a relatively small and simple device, it is useful as a base sequence determination method for DNA in the clinical field, and in particular as a base sequence determination method for DNA in medical treatments that are tailor-made according to the genomic information of each patient, one by one.

The invention claimed is:

1. A method for determining the base sequence of a DNA, comprising:
   (a) the step of ligating a DNA to be analyzed, wherein said DNA has a one base-protruding end and is immobilized on a support, and a probe by a DNA ligase, wherein said probe has a one base-protruding end and an identification-label according to the species of the base at the protruding end, and said probe contains a recognition sequence of a restriction enzyme whose recognition sequence is apart from a cleavage site;
   (b) the step of identifying the species of the identification label of said probe that has been ligated to said DNA to be analyzed by single molecule observation; and
   (c) the step of cleaving a ligated DNA of said DNA to be analyzed and said probe by said restriction enzyme whose recognition sequence is apart from the cleavage site.

2. The method according to claim 1, wherein said probe includes four species of probe having a one base-protruding end complementary respectively to A, T, C or G.

3. The method according to claim 1, wherein the distance between the recognition sequence for said restriction enzyme and the protruding end on said probe is one base shorter than the distance between the recognition sequence and the cleavage site for said restriction enzyme.

4. The method according to claim 1, wherein each of the steps is carried out by a chain reaction.

5. The method according to claim 1, wherein said identification label is a fluorescent label, a quantum dot or a metal colloid.

6. The method according to claim 5, wherein identification of the species of said identification label is carried out by detection of fluorescence wavelength of said fluorescent label.

7. The method according to claim 6, wherein the detection of the fluorescence wavelength is carried out using a single molecule fluorescence spectromicroscope.

8. The method according claim 1, wherein the base sequences of a plurality of DNAs to be analyzed are determined simultaneously.

9. The method according to claim 1, wherein said restriction enzyme is an enzyme that generates a one base-protruding end.

10. The method according to claim 9, wherein said enzyme is a class IIS restriction enzyme.

11. The method according to claim 1, wherein the protruding end of said DNA to be analyzed and the protruding end of said probe are both 3' protruding ends.

12. The method according to claim 1, wherein said restriction enzyme is an enzyme that generates a one base-protruding end at the 3' end.

13. The method according to claim 12, wherein said enzyme is selected from BmrI, BmuI, BfiI, AsuHPI, HphI, BciVI, BfuI, HpyAV, MboII, NcuI and MnlI.

14. The method according to claim 1, wherein the protruding end of said DNA to be analyzed and the protruding end of said probe are both 5' protruding ends.

15. The method according to claim 1, wherein said restriction enzyme is an enzyme that generates a one base-protruding end at the 5' end.

16. The method according to claim 15, wherein said enzyme is selected from AclWI, AlwI, BinI, BspPI, BstH9I, Bst31TI, EacI, BccI, HpyC1I, BcefI, PleI and PpsI.

17. The method according to claim 1, wherein said support is formed from a material that is transparent to light.

18. A probe, which is a probe having a one base-protruding end and an identification-labeled according to the species of the base at the protruding end, containing a recognition sequence of a restriction enzyme whose recognition sequence is apart from a cleavage site.

19. The probe according to claim 18, wherein the distance between said recognition sequence and said one-base-protruding end is one base shorter than the distance between said recognition sequence and said cleavage site.

20. The probe according to claim 18, wherein said protruding end is a 3' protruding end.

21. The probe according to claim 18, wherein said protruding end is a 5' protruding end.

22. The probe according to claim 18, wherein said recognition sequence is a recognition sequence of a class IIS restriction enzyme.

23. A kit for determining the base sequence of a DNA, containing the probe according to claim 18, wherein said probe includes four species of probe having a one base-protruding end complementary respectively to A, T, C or G.

24. The kit according to claim 23, further containing a restriction enzyme and a DNA ligase.

* * * * *